(12) United States Patent
Deppermann

(10) Patent No.: US 7,685,768 B2
(45) Date of Patent: Mar. 30, 2010

(54) AUTOMATED TESTING OF SEEDS

(75) Inventor: Kevin L. Deppermann, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1133 days.

(21) Appl. No.: 11/213,433

(22) Filed: Aug. 26, 2005

(65) Prior Publication Data
US 2006/0042528 A1 Mar. 2, 2006

Related U.S. Application Data

(60) Provisional application No. 60/604,628, filed on Aug. 26, 2004.

(51) Int. Cl.
*A01C 1/00* (2006.01)
(52) U.S. Cl. ...................................... 47/58.1 SE; 47/14
(58) Field of Classification Search ...................... 435/4, 435/6
See application file for complete search history.

(56) References Cited

U.S. PATENT DOCUMENTS

| | | |
|---|---|---|
| 2,756,903 A | 7/1956 | Kreidler |
| 3,530,372 A | 9/1970 | Laukien |
| 3,642,128 A | 2/1972 | Westwood et al. |
| 3,861,788 A | 1/1975 | Webster |
| 4,037,970 A | 7/1977 | Webster et al. |
| 4,040,747 A | 8/1977 | Webster |
| 4,260,262 A | 4/1981 | Webster |
| 4,375,854 A | 3/1983 | Hedel |
| 4,480,765 A | 11/1984 | Tonus |
| 4,654,592 A | 3/1987 | Zens |
| 4,734,584 A | 3/1988 | Rosenthal |
| 4,752,689 A | 6/1988 | Satake |
| 4,818,380 A | 4/1989 | Azegami et al. |
| 4,884,696 A | 12/1989 | Peleg |
| 4,931,061 A | 6/1990 | Young |
| 4,946,046 A | 8/1990 | Affleck et al. |
| 5,051,699 A | 9/1991 | Hanawa et al. |
| 5,067,631 A | 11/1991 | Baba |
| 5,132,538 A | 7/1992 | Norris |
| 5,221,518 A | 6/1993 | Mills |

(Continued)

FOREIGN PATENT DOCUMENTS

CL 673-03 2/2004

(Continued)

OTHER PUBLICATIONS

"Seed Meister Luminar 3076," Brimrose Corporation of America, Baltimore, MD, http://www.brimrose.com/seed_meister.html.

(Continued)

*Primary Examiner*—Francis T Palo
(74) *Attorney, Agent, or Firm*—James E. Davis; Joseph A. Schaper; Harness, Dickey & Pierce, P.L.C.

(57) ABSTRACT

An apparatus for the automated testing of seeds includes a testing device having a testing stage, for analyzing a seed delivered to the testing stage; and a conveyor for automatically individually conveying each of a plurality of seeds in a tray between individual compartments in the tray and the testing stage of the testing device.

39 Claims, 5 Drawing Sheets

U.S. PATENT DOCUMENTS

| | | |
|---|---|---|
| 5,245,188 A | 9/1993 | Satake et al. |
| 5,253,302 A | 10/1993 | Massen |
| 5,321,212 A | 6/1994 | Wadell |
| 5,412,220 A | 5/1995 | Moore |
| 5,475,221 A | 12/1995 | Wang |
| 5,533,145 A | 7/1996 | Shofner et al. |
| 5,590,791 A | 1/1997 | Gschweitl |
| 5,668,374 A | 9/1997 | DiFoggio et al. |
| 5,669,511 A | 9/1997 | Satake et al. |
| 5,733,592 A | 3/1998 | Wettstein et al. |
| 5,751,421 A | 5/1998 | Wright et al. |
| 5,764,819 A | 6/1998 | Orr et al. |
| 5,833,947 A | 11/1998 | Rocklage et al. |
| 5,836,438 A | 11/1998 | Jung |
| 5,837,458 A | 11/1998 | Minshull et al. |
| 5,864,984 A | 2/1999 | McNertney |
| 5,918,977 A | 7/1999 | Borggaard et al. |
| 5,991,025 A | 11/1999 | Wright et al. |
| 6,098,838 A | 8/2000 | Saho et al. |
| 6,100,526 A | 8/2000 | Mayes |
| 6,150,158 A | 11/2000 | Bhide et al. |
| 6,237,286 B1 | 5/2001 | Williames |
| 6,266,864 B1 | 7/2001 | Barber |
| 6,397,678 B1 | 6/2002 | Popper |
| 6,537,826 B1 * | 3/2003 | Horigane .................... 436/176 |
| 6,640,428 B2 | 11/2003 | Barber |
| 6,646,264 B1 * | 11/2003 | Modiano et al. ....... 250/339.07 |
| 6,688,037 B2 | 2/2004 | Keller et al. |
| 6,705,827 B2 | 3/2004 | Keller et al. |
| 6,706,989 B2 | 3/2004 | Hunter et al. |
| 6,782,991 B2 | 8/2004 | Johansson |
| 6,809,819 B1 | 10/2004 | Vinjamoori et al. |
| 6,879,389 B2 | 4/2005 | Meyer et al. |
| 6,959,617 B2 | 11/2005 | Deppermann |
| 7,044,306 B2 | 5/2006 | Deppermann |
| 7,258,237 B2 | 8/2007 | Nielsen |
| 7,367,155 B2 | 5/2008 | Kotyk et al. |
| 7,502,113 B2 | 3/2009 | Deppermann et al. |
| 2001/0013486 A1 | 8/2001 | Yamakawa |
| 2001/0014750 A1 | 8/2001 | Ulrich et al. |
| 2002/0144458 A1 | 10/2002 | Hunter et al. |
| 2003/0142852 A1 | 7/2003 | Lu et al. |
| 2004/0072143 A1 | 4/2004 | Timmis et al. |
| 2004/0141641 A1 | 7/2004 | McDonald et al. |
| 2004/0160607 A1 | 8/2004 | Lin et al. |
| 2004/0221335 A1 | 11/2004 | Shewmaker |
| 2005/0082207 A1 | 4/2005 | Deppermann |
| 2006/0042527 A1 | 3/2006 | Deppermann |
| 2006/0042528 A1 * | 3/2006 | Deppermann ............... 111/171 |
| 2006/0046244 A1 | 3/2006 | Deppermann |
| 2006/0112628 A1 | 6/2006 | Kotyk et al. |
| 2007/0048872 A1 | 3/2007 | Deppermann et al. |
| 2007/0204366 A1 | 8/2007 | Deppermann et al. |
| 2007/0207485 A1 | 9/2007 | Deppermann et al. |
| 2007/0240242 A1 | 10/2007 | Modiano et al. |
| 2008/0000815 A1 | 1/2008 | Deppermann |
| 2008/0113367 A1 | 5/2008 | Becker et al. |
| 2008/0131254 A1 | 6/2008 | Cope et al. |
| 2008/0131924 A1 | 6/2008 | Cope et al. |
| 2008/0317279 A1 | 12/2008 | Deppermann et al. |
| 2009/0032441 A1 | 2/2009 | Corak et al. |

FOREIGN PATENT DOCUMENTS

| | | |
|---|---|---|
| CL | 2189-05 | 5/2007 |
| DE | 19845883 A1 | 5/1999 |
| DE | 102004063769 A1 | 7/2006 |
| EP | 0636310 A1 | 2/1995 |
| EP | 0730164 | 9/1996 |
| EP | 0750188 | 12/1996 |
| EP | 0511184 B1 | 6/1998 |
| EP | 0539537 B2 | 12/2000 |
| FR | 2549963 | 2/1985 |
| GB | 1355612 | 6/1974 |
| JP | 401156233 A | 6/1989 |
| JP | 406284806 A | 10/1994 |
| JP | 10319106 | 4/1998 |
| WO | WO 9624830 | 8/1996 |
| WO | WO 9700887 | 1/1997 |
| WO | WO 9844140 | 10/1998 |
| WO | WO 9940419 | 8/1999 |
| WO | WO 9941383 | 8/1999 |
| WO | WO 9958959 | 11/1999 |
| WO | WO 0052990 | 9/2000 |
| WO | WO 0071993 A1 | 11/2000 |
| WO | WO-01/22043 | 3/2001 |
| WO | WO 01/22043 A2 | 3/2001 |
| WO | WO 0144828 A1 | 6/2001 |
| WO | WO 0189288 A1 | 11/2001 |
| WO | WO 0259586 | 1/2002 |
| WO | WO 0216090 A3 | 2/2002 |
| WO | WO 02/48687 | 6/2002 |
| WO | WO-02/071040 | 9/2002 |
| WO | WO-2006/026467 | 3/2006 |

OTHER PUBLICATIONS

Archibald et al., "Development of Short-Wavelength Near-Infrared Spectral Imaging for Grain Color Classification," SPIE vol. 3543, 1998, pp. 189-198.

Bauman, et al., Inheritance of Variation of Oil Content of Individual Corn Kernels, Crop Science, vol. 5, pp. 137-138, 1965.

Daun et al., "Comparison of Three Whole Seed Near-Infrared Analyzers for Measuring Quality Components of Canola Seed," vol. 71, No. 10, 1994, pp. 1063-1068.

Delwiche, "Single Sheat Kernel Analysis by Near-Infrared Transmittance: Protein Content," Analytical Techniques and Instrumentation, vol. 72, No. 1, 1995, pp. 11-16.

Dowell et al., "Automated Single Wheat Kernel Quality Measurement Using Near-Infrared Reflectance," ASAE Annual International Meeting, 1997, paper No. 973022.

Dowell, "Automated Color Classification of Single Wheat Kernels Using Visible and Near-Infrared Reflectance," Cereal Chemistry, vol. 75(1), 1998, pp. 142-144.

Dr. Jolanta Soos, "Industrial Process Monitoring Requires Rugged AOTF Tools," Laser Focus World, Aug. 1994.

Floyd E. Dowell, "An Intelligent Automated System for Determining Peanut Quality," IEEE International Workshop on Intelligent Robots and Systems, Jul. 1990.

Gambhir, et al., Simultaneous Determination of Moisture and Oil Content in Oilseeds by Pulsed Muclear Magnetic Resonance, JOACS, vol. 62, No. 1, Jan. 1985.

Guy Rubel, "Simultaneous Determination of Oil and Water Contents in Different Oil Seeds by Pulsed Nuclear Magnetic Resonance," XP 001080188, JAOCS, vol. 71, No. 10, Oct. 1994.

J.M. Halloin et al., "Proton Magnetic Resonance Imaging of LIpd in Pecan Embryos", XP 001080187, Journal of the American Oil Chemists' Society, vol. 70, No. 12, Dec. 1993.

J.R. Heil, et al., "Magnetic Resonance Imaging and Modeling of WaterUp-take into Dry Beans", XP 002202044, Dept. of Food Science and Technology, University of California, Davis, CA, Jan. 23, 1992.

K. Saito, et al., "Application of Magnetic Resonance Imaging to Non-Destructive Boid Detection in Watermelon," XP 000656797, Cryogenics, vol. 36, No. 12, 1996.

M.R. Lakshiminarayana et al., "Spatial distribution of oil in groundnut and sunflower seeds by nuclear magnetic resonance imaging," XP 002201726, J. Biosci., vol. 17, No. 1, Mar. 1992, pp. 87-93.

MacNamara, et al., "Multiplex Sample NMR: an Approach to High-Throughput NMR Using a Parallel Coil Probe," Analytica Chimica Acta; vol. 397, No. 1/03; Elsevier Science B.V.; Oct. 1999, pp. 9-16.

Massie and Norris, "Spectral Reflectance and Transmittance Properties of Grain in the Visible and Near Infrared", Transactions of the ASAE, Winter Meeting of the American Society of Agricultural Engineers, 1965, pp. 598-600.

McEntyre, et al., Comparison of Water Absorption Patterns in Two Barley Cultivars, Using Magnetic Resonance Imaging, AACCI, Cereal Chemistry, vol. 76, No. 6, pp. 792-795, 1998.

McGinty, et al., A System for Automatic Weight Determination of Individual Grain Kernels: Principles and Evaluation, Cereal Science Today, vol. 19, No. 5, May 1974.

Orman and Schumann, "Comparison of Near-Infrared Spectroscopy Calibration Methods for the Prediction of Protein, Oil, and Starch in Maize Grain," J. Agric. Food Chem. vol. 39, 1991, pp. 883-886.

P.A. Hailey—Pfizer Central Research, "The Role of NIR Spectroscopy in the Measurement of Pharmaceutical Manufacture," http://www.brimrose.com/hailey.html; date unknown.

Paige, et al., "Apparatus for Automatic Measurement of Kernel Weight, Length, and Thickness," Crop Science, vol. 31, pp. 1314-1318, 1991.

Robutti, "Maize Kernel Hardness Estimation in Breeding by Near-Infrared Transmission Analysis," Analytical Techniques and Instrumentation vol. 72, No. 6, 1995, pp. 632-636.

Sander, et al., System for Automatic Weight Determination of Individual Grain Kernels, Transactions of the American Society Agricultural Engineers, vol. 16, No. 6, pp. 1146-1147, Nov./Dec. 1973.

Siebenmorgen, et al., A Data Acquisition/Control System for Individual Kernel and Thin-Layer Grain Drying Research, The American Society of Agricultural Engineers, No. 91-3042, Jun. 1991.

Song et al., Non-invasive Measurement of Moisture Distribution in Individual Wheat Kernels by Magnetic Resonance Imaging, SPIE vol. 2345, Nov. 2-4, 1994.

Yoshida, et al., "An Automatic Sequential Single-Seed Weighing System: Variation in Soybean Seed Weight," Journal of the Faculty of Agriculture, Hokkaido University, vol. 61, Pt. 2, 1983.

* cited by examiner

US 7,685,768 B2

AUTOMATED TESTING OF SEEDS

CROSS REFERENCE TO RELATED APPLICATIONS

This application claims priority to U.S. Provisional Application Ser. No. 60/604,628, filed Aug. 26, 2004, the entire disclosure of which is incorporated herein by reference.

BACKGROUND OF THE INVENTION

This invention relates to the testing of seeds, and in particular to the automating of testing of seeds.

In developing high performance seeds, it is often desirable to ensure that each seed in a given population exhibits a particular characteristic. For example in the development of corn seeds, it might be desirable to ensure that each seed in the population has a given oil content, e.g. an oil content of at least 5-6 percent. One method of non-destructively determining characteristics of a seed such as the oil content of a seed is through analysis of the seed, and in particular nmr testing of the seed. It would be very time consuming and tedious, and thus very expensive, to individually test each seed in a large population manually, and thus most seed development programs rely upon testing of representative samples of the population, however, because of the variations among seeds even from the same plants, representative sampling is not as effective as testing all seeds.

SUMMARY OF THE INVENTION

The present invention provides apparatus and methods for automating the testing of each seed in a large population, thereby improving the development of high performance seeds.

One preferred embodiment of an apparatus constructed according to the principles of this invention generally comprises a testing device having a testing stage, for analyzing a seed delivered to the testing stage; and a conveyor for automatically individually conveying each of a plurality of seeds in a tray between individual compartments in the tray and the testing stage of the testing device.

One preferred embodiment of a method according to the principles of this invention generally comprises the steps of disposing the seeds in individual compartments in a seed tray; and successively conveying each seed from its compartment in the seed tray to a testing device; testing the seed; and conveying the seed back to its compartment in the tray.

BRIEF DESCRIPTION OF THE DRAWINGS

Corresponding reference numerals indicate corresponding parts throughout the several views of the drawings.

DETAILED DESCRIPTION

Figure 1:
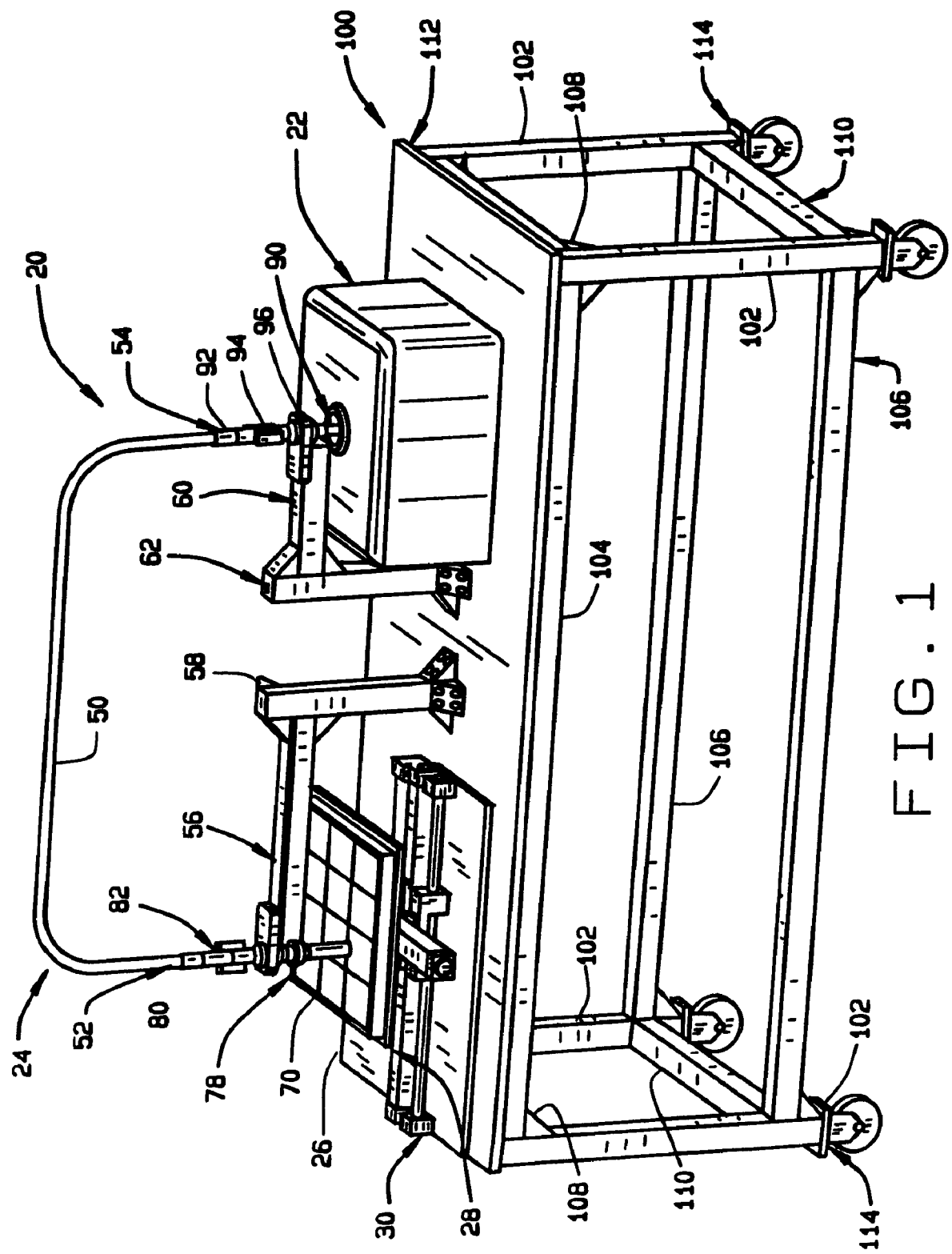
FIG. 1 is a perspective view of a preferred embodiment of an automated testing system constructed according to the principles of this invention.
Figure 2:
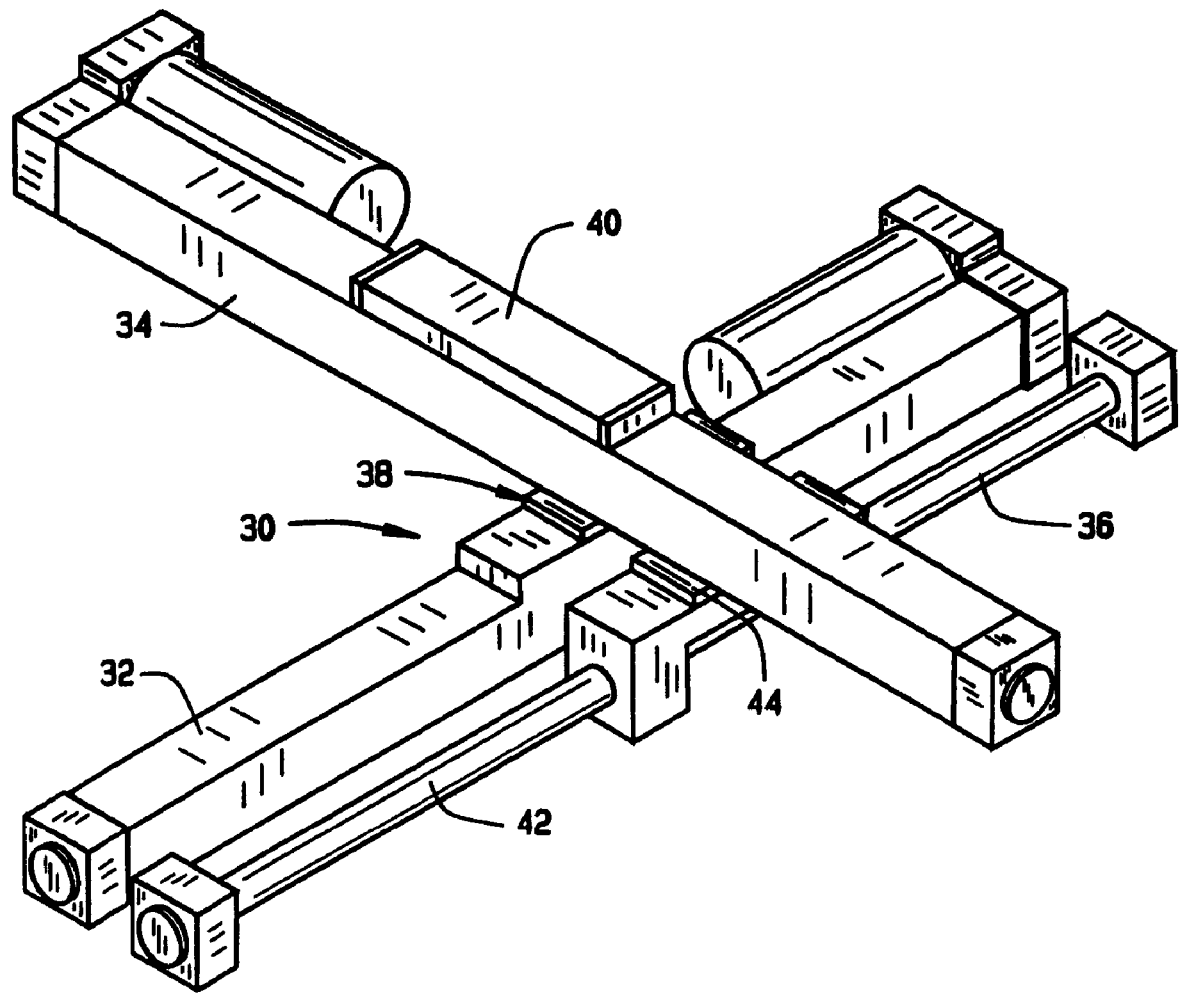
FIG. 2 is a perspective view of the two dimensional translation system employed in the preferred embodiment of the automated testing system.

A preferred embodiment of an apparatus for the testing of seeds constructed according to the principles of this invention is indicated generally as 20 in FIG. 1. Generally, the apparatus 20 comprises a testing device 22, having a testing stage, for analyzing a seed delivered to the testing stage; and a conveyor 24 for automatically individually conveying each of a plurality of seeds in a tray 26 between individual compartments in the tray and the testing stage of the testing device 22.

In this preferred embodiment, the testing device 22 is an Nuclear Magnetic Resonance (NMR) testing device, such as a MARAN Ultra Low Resolution NMR available from Resonance Instruments Ltd. While in this preferred embodiment the testing device is an NMR testing device, the invention is not so limited, and the testing could be some other type of testing device, such as spectral imaging device, etc.

The apparatus 20 preferably also includes a seed tray support, such as stage 28 for supporting one or more seed trays 26. The stage 28 is preferably mounted on a two-directional positioner 30 for selectively bringing the compartments of the supported seed trays 26 into alignment with a first end of the seed conveyor 24. The two-directional positioner 30 preferably comprises a first linear positioner 32, a second linear positioner 34, and slide 36. The first linear positioner 32 has translating carriage 38 that moves as the positioner operates, and the second linear positioner 34 has a translating carriage 40 that moves as the positioner operates. The slide 36 has a rail 42 and a carriage 44 that slides on the rail. The second linear positioner 34 is mounted on the carriage 38 of the first linear positioner, and the carriage 44 of the slide 36, so that the second carriage translates in a first direction parallel to the axis of the first linear positioner 32. The stage 28 is mounted on the carriage 40 of the second linear positioner 34, so that the stage translates in a second direction parallel to the axis of the second linear positioner. A controller can operate the positioners 32 and 34 of the two-directional positioner 30 to successively bring each compartment of each of the trays 26 mounted on the stage 28 into alignment with the first end 30 of the conduit.

The seed conveyor 24 comprises a conduit 50 having a first end 52 adjacent the trays and a second end 54 adjacent the testing device 22. The first end 52 of the conduit 50 is preferably mounted in a fixed position, so that movement of the stage 28 brings individual compartments of the trays into a alignment with the end of the conduit. (Alternatively, the first end 52 can be mounted to move relative to the compartments of the trays, and the end moved into alignment with each compartment). As shown in FIG. 1 the first end 52 of the conduit can be held by a mounting arm 56, extending generally horizontally from a generally vertical post 58. The second end 54 of the conduit 50 is preferably mounted in a fixed position relative to the testing device 22. As shown in FIG. 1, the second end can be held in a mounting arm 60 extending generally horizontally from a generally vertical support 62, in a fixed location.

Figure 3:
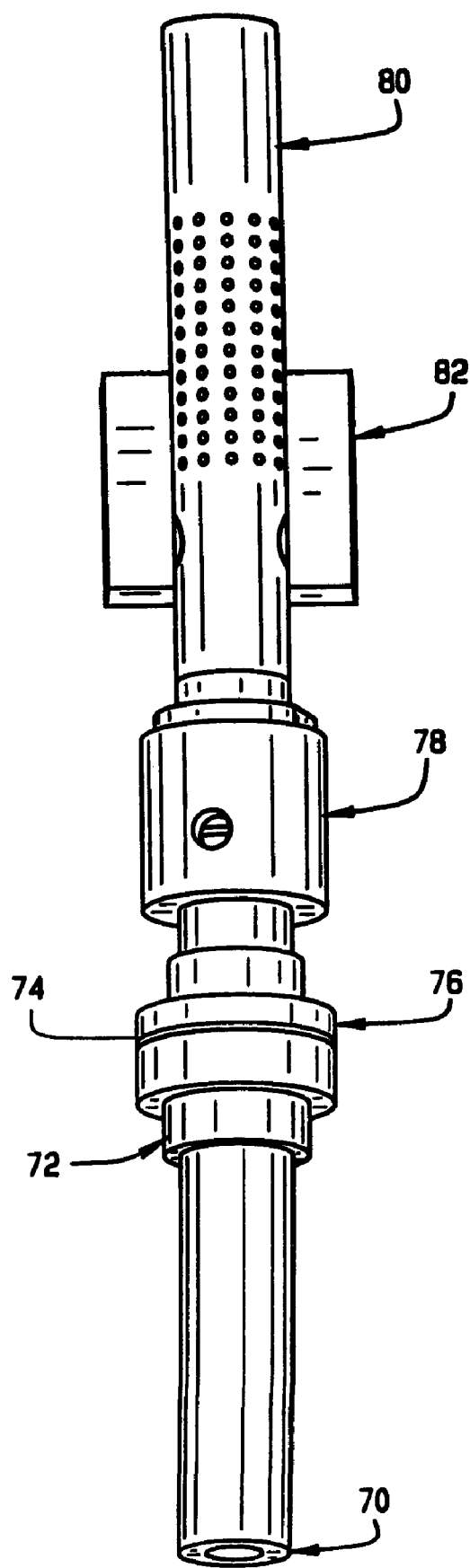
FIG. 3 is a perspective view of the first end of the seed conveyor in the preferred embodiment of the automated testing system.

As shown in FIG. 3, the first end 52 of the conduit 50 comprises a seed tube 70, a magnet bottom 72, a magnet ring 74, and a magnet top 76. An air amplifier 78 is positioned above this assembly, and a seed sensor tube 80, with seed sensors 82 mounted thereon, is positioned about the air amplifier 78. The air amplifier 78 is adapted to be operated with the application of compressed air to create an air flow in the conduit 50 toward the second end 54. This air flow helps entrain and carry a seed from the compartment in tray 26 aligned with the first end 52 of the conduit, and also helps to brake the movement of the seed from the testing device 22 back to the compartment in the tray 26, to reduce the risk of damage to the seed.

Figure 4:
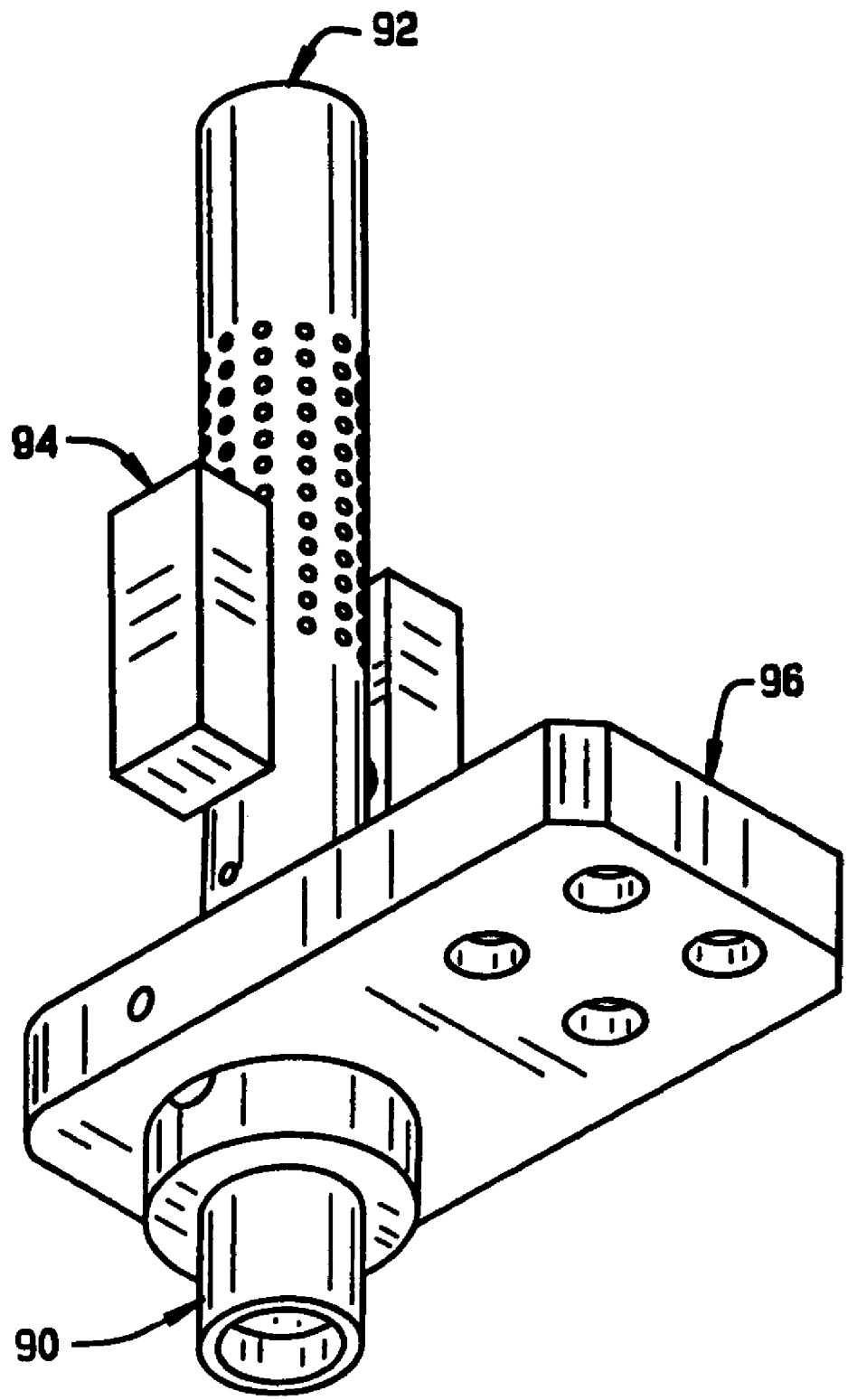
FIG. 4 is a perspective view of the second end of the seed conveyor in the preferred embodiment of the automated testing system.
Figure 5:
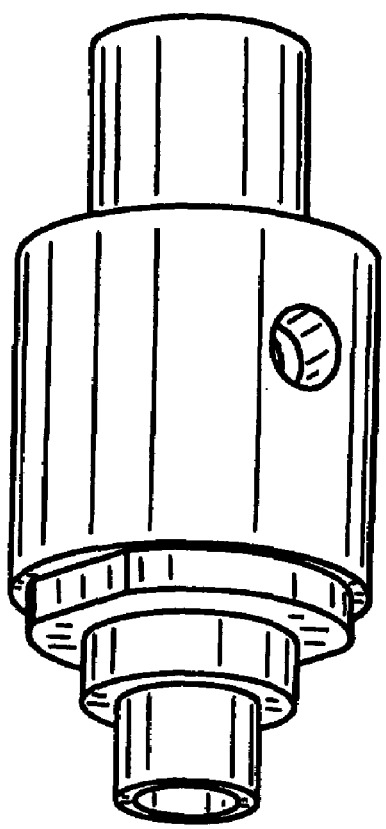
FIG. 5 is a perspective view of an air amplifier used in the seed conveyor of the preferred embodiment of the automated testing system.
Figure 6:
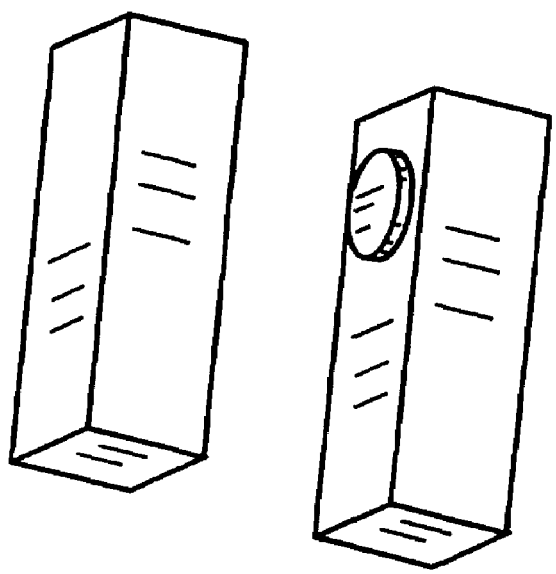
FIG. 6 is a perspective view of the seed sensors used in the seed conveyor of the preferred embodiment of the automated testing system.

As shown in FIG. 4, the second end 54 of the conduit 50 comprises an air amplifier 90, a seed sensor tube 92, with seed sensors 94 mounted thereon, is positioned about the air amplifier 90. The second end 54 also includes a bracket 96 for mounting the second end on the arm 60. The air amplifier 90 is adapted to be operated with the application of compressed air to create an air flow in the conduit 50 toward the first end 52. This air flow helps entrain and carry a seed from the testing device 22 to the compartment in tray 26 aligned with the first end 52 of the conduit, and also helps to brake the movement of the seed from the tray 26 to the testing device 22, to reduce the risk of damage to the seed.

As indicated above, the seeds are preferably disposed in individual compartments in one or more seed trays 26. The process of loading the seeds into compartments in tray 26 can also be automated, if desired.

As shown in FIG. 1, in the first preferred embodiment the apparatus 20 is conveniently carried on a wheeled cart 100, having four vertical posts 102 connected by upper and lower longitudinal members 104 and 106, at the front and back, and upper and lower transverse members 108 and 110 at the left and right sides, and a table top 112 mounted therein. A caster 114 can be mounted at the bottom of each post 102 to facilitate moving the cart 100. The details of the construction of the cart 100 are not critical to the invention, and thus the cart 100 could have some other configuration, or some other structure can be provided to support the apparatus 20 without departing from the principles of this invention.

Operation

In operation, a control operates the linear positioners 32 and 34 to bring a particular compartment of tray 26 into alignment with the first end 52 of the conduit 50 of the seed conveyor 24. The control operates the air amplifier 78 to initiate an air flow through the conduit 50 toward the second end 54. The air flow lifts the seed out of the compartment in tray 26 and carries it through the conduit 50 toward the second end 54. The control then operates the air amplifier 90 to create an air flow from the second end 54 toward the first end 52, to slow the seed. The sensors 82 and 94 detect the position of the seed before it reaches the end of the conduit 50. The seed is preferably slowed sufficiently so that it drops into the testing chamber of the testing device 22 without damaging the seed. In the preferred embodiment, the seed is actually stopped before reaching the second end of the conduit 52, and drops under gravity into the testing chamber. When the analysis is completed, the control operates the air amplifier 90 to create an air flow from the second end 54 toward the first end 52. The air flow lifts the seed out of the testing chamber of the testing device 22 and carries it through conduit 50 toward the first end 52 of the conduit. The control then operates the air amplifier 78 to create an air flow from the first end 52 toward the second end 54, to slow the seed. The seed is preferably slowed sufficiently so that it drops into the compartment of tray 26 without damaging the seed. In the preferred embodiment, the seed is actually stopped before reaching the first end of the conduit 50, and drops under gravity into the compartment in the tray. The control then operates linear positioners to bring the next compartment into alignment with the first end 50, and the process is repeated.

Thereafter the test data for each seed can be correlated with location within the tray, and the seeds having the desired characteristic can be separated from the seeds that do not have the desired characteristic. This can be a simple separation into the groups, those with and those without the desired characteristic, or it can be a separation into multiple groups each exhibiting a different characteristic or different degrees of the same characteristic.

The controller that controls the movement of the table can output position information to correlate the seed location with test data. Alternatively, position sensors can be used to provide position information to correlate the seed location with test data.

What is claimed is:

1. A method for the automated testing of individual seeds, the method comprising:
   disposing the seeds in individual compartments in a seed tray;
   successively conveying a seed from its compartment in the seed tray to a testing device;
   testing the seed; and
   conveying the seed back to its compartment in the seed tray.

2. The method according to claim 1 wherein the testing is nmr testing with an nmr testing device.

3. The method according to claim 2 wherein the step of conveying a seed from its compartment in the seed tray to a testing device comprises pneumatically conveying the seed from its compartment in the seed tray to the nmr testing device.

4. The method according to claim 3 wherein the step of conveying the seed back to its compartment in the tray comprises pneumatically conveying the seed from the nmr testing device to its compartment.

5. The method according to claim 4 wherein the steps of pneumatically conveying a seed from its compartment in the seed tray to an nmr testing device and pneumatically conveying the seed back to its compartment in the tray are performed with a pneumatic conveyor having a fixed first end and a fixed second end adjacent the nmr testing device.

6. The method according to claim 5 wherein the compartments of the seed tray are successively aligned with the fixed first end of the pneumatic conveyor.

7. The method according to claim 6 wherein each seed tray is mounted on a table and wherein the table is moved to bring each compartment into alignment with the fixed first end of the pneumatic conveyor.

8. The method according to claim 7 comprising storing information about the nmr seed test with information relating to the seed location.

9. The method according to claim 6 wherein the seed tray is mounted on a table, and wherein the table is moved with a two-dimensional positioner.

10. The method according to claim 9 further comprising storing information about the nmr test of a seed in association with information about the seed location from the two-dimensional positioner.

11. The method according to claim 6 wherein the step of conveying a seed from its compartment to the nmr testing device comprises inducing an air flow in a conduit to draw a seed from its compartment and propel it toward the nmr testing device.

12. The method according to claim 11 wherein the step of inducing an air flow in the conduit employs a venturi.

13. The method according to claim 11 further comprising slowing the seed in the conduit before it reaches the nmr testing device.

14. The method according to claim 13 wherein the step of slowing the seed in the conduit before it reaches the nmr testing device comprises inducing an air flow in the conduit to slow the seed.

15. The method according to claim 6 wherein the step of conveying the seed from the nmr testing device to its compartment in the tray comprises inducing an air flow in a conduit to draw the seed from the nmr testing device and propel it toward its compartment in the tray.

16. The method according to claim 15 wherein the step of inducing an air flow in the conduit employs a venturi.

17. The method according to claim 15 further comprising slowing the seed in the conduit before it reaches its compartment.

18. The method according to claim 17 wherein the step of slowing the seed in the conduit before it reaches its compartment comprises inducing an air flow in the conduit to slow the seed.

19. The method according to claim 6 wherein the step of conveying a seed from its compartment to the nmr testing device comprises inducing an air flow in a conduit extending between the compartment and the nmr testing device, and wherein the step of conveying the seed from the nmr testing device to its compartment comprises inducing an air flow in a conduit extending between the compartment and the nmr testing device.

20. The method according to claim 6 further comprising storing information relating to the nmr test of the seed in association with information about the location of the seed.

21. The method of claim 20 wherein the information about the seed is information from a positioning system that positions the seed tray.

22. The method of claim 20 wherein the information about the seed is derived from information from a positioning system that positions the seed tray.

23. The method according to claim 2 wherein the step of conveying the seed back to its compartment in the tray comprises pneumatically conveying the seed from the nmr testing device to its compartment.

24. The method according to claim 1 further comprising:
moving the seed tray to successively bring the compartments of the seed tray into alignment with a first end of a conduit; and
successively conveying each seed in the seed tray from its compartment in the seed tray to the testing device through the conduit; testing each seed; and conveying each seed back to its compartment in the seed tray through the conduit.

25. The method according to claim 1 wherein:
testing the seed includes testing the seed with an nmr testing device;
conveying a seed from its compartment in the seed tray to a testing device includes pneumatically conveying a seed from its compartment in the seed tray to an nmr testing device via a conduit, the conduit having a fixed first end and a fixed second end adjacent the nmr testing device; and
conveying the seed back to its compartment includes pneumatically conveying the seed back to its compartment in the tray via the conduit.

26. The method according to claim 1 wherein conveying a seed from its compartment in the seed tray to a testing device comprises pneumatically conveying the seed from its compartment in the seed tray to the testing device.

27. The method according to claim 26 wherein conveying the seed back to its compartment in the seed tray comprises pneumatically conveying the seed from the testing device back to its compartment in the seed tray.

28. The method according to claim 1 wherein conveying a seed from its compartment in the seed tray and conveying the seed back to its compartment in the seed tray are performed with a pneumatic conveyor having a fixed first end, and a fixed second end adjacent the testing device.

29. The method according to claim 28 further comprising successively aligning the compartments of the seed tray with the fixed first end of the pneumatic conveyor.

30. The method according to claim 29 wherein each seed tray is mounted on a table, the method further comprising moving the table to bring each compartment of the seed tray into alignment with the fixed first end of the pneumatic conveyor.

31. The method according to claim 1 wherein the seed tray is mounted on a table, the method further comprising moving the table with a two-dimensional positioner.

32. The method according to claim 1 wherein conveying a seed from its compartment in the seed tray comprises inducing an air flow in a conduit to draw a seed from its compartment in the seed tray.

33. The method according to claim 32 wherein inducing an air flow in the conduit employs a venturi.

34. The method according to claim 32 further comprising slowing the seed in the conduit before it reaches the testing device.

35. The method according to claim 34 wherein slowing the seed in the conduit before it reaches the testing device comprises inducing an air flow in the conduit to slow the seed.

36. The method according to claim 1 further comprising storing information relating to the test of the seed in association with information about a location of the seed in the seed tray.

37. The method according to claim 1 further comprising:
aligning a seed conveyor and an individual compartment of the seed tray; and
conveying a seed with the seed conveyor from said individual compartment in the seed tray to the testing device; testing the seed; and conveying the seed with the seed conveyor back to said individual compartment in the seed tray.

38. A method for the automated testing of seeds, the method comprising:
conveying a seed from a compartment in a multi-compartment seed tray to a testing device;
testing the seed; and
conveying the seed back to its compartment in the multi-compartment seed tray.

39. The method according to claim 38 further comprising:
aligning a seed conveyor and said compartment in the multi-compartment seed tray; and
conveying the seed with the seed conveyor from said compartment in the multi-compartment seed tray to the testing device; testing the seed; and conveying the seed with the seed conveyor back to said compartment in the multi-compartment seed tray.

* * * * *